United States Patent [19]

Matas et al.

[11] Patent Number: 4,736,037
[45] Date of Patent: Apr. 5, 1988

[54] 2-HALO-ARYL-PYRIDINEMETHANOLS WITH ANALGESIC OR ANTIINFLAMMATORY ACTIVITY

[75] Inventors: Ricardo D. Matas; Jose M. C. Puigmarti; Jose M. Repolles; Jorge S. Sera, all of E-Barcelona, Spain

[73] Assignee: Lacer, S.A., Barcelona, Spain

[21] Appl. No.: 878,579

[22] Filed: Jun. 26, 1986

Related U.S. Application Data

[62] Division of Ser. No. 225,019, Jan. 14, 1981, Pat. No. 4,614,833.

[30] Foreign Application Priority Data

Jan. 16, 1980 [EP] European Pat. Off. ............ 80100207

[51] Int. Cl.$^4$ .................................. C07D 213/30
[52] U.S. Cl. .......................... 546/344; 546/314; 546/315
[58] Field of Search .......................... 546/344

[56] References Cited

U.S. PATENT DOCUMENTS 4,304,941 12/1981 Lee et al. ............ 546/315

Primary Examiner—Alan L. Rotman

Attorney, Agent, or Firm—Oblon, Fisher, Spivak, McClelland & Maier

[57] ABSTRACT

2-Halo-pyridine of the formula:

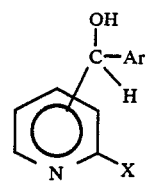

wherein X is Cl or Br; Ar is phenyl or substituted phenyl of the formula

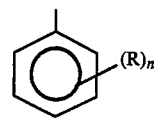

in which n is 0, 1, 2 or 3; R is $C_{1-4}$ alkyl, $C_{1-4}$ alkoxy, phenoxy, $C_{1-4}$ alkylthio, halogen, OH or $C_6H_5$; or a pharmaceutically acceptable salt thereof.

4 Claims, No Drawings

2-HALO-ARYL-PYRIDINEMETHANOLS WITH ANALGESIC OR ANTIINFLAMMATORY ACTIVITY

This is a division of copending prior application Ser. No. 225,019, filed on Jan. 14, 1981, now U.S. Pat. No. 4,614,833, issued Sept. 30, 1986.

The invention relates to new pharmacologically active 2-halo-pyridines of the general formula

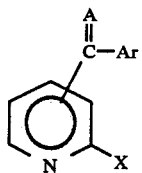

(I)

Wherein
X: Cl, Br
A: =O

Ar:

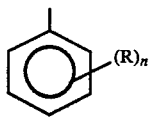

n=0, 1, 2, 3
R=alkyl $C_{1-4}$, alkoxy $C_{1-4}$, phenoxy, alkylthio $C_{1-4}$, halogen, OH, $C_6H_5$.

and their salts, addition compounds and precursors (prodrugs). By precursors it is understood every pharmaceutically acceptable bioprecursor; that is compounds derived from those of Formula I, like esters or imines, which are split in an animal body by chemical or enzymatic processes, and without modifying qualitatively the biological activity of the compounds from which they derive.

The alkyl groups in the various definitions of R are especially methyl, ethyl, propyl, isopropyl, butyl, tert-butyl, i-butyl or sec-butyl. Halogen is F, Cl, Br and I, especially F and Cl. The substitution of R is in 2, 3, 4, 5 or 6 position, if n=1. If n=2, the 2,4-and 2,5-positions are preferred, although also 2,6-, (3,6- or 4,6-) positions are suitable. For n=3, the 2, 4, 6- and 2, 3, 5-substitution is preferred. The residues R may be the same or different, if n=2 or 3.

The substitution of

on the pyridine nucleus may be in 3, 4, 5 or 6 position, taking as the 2-position that of halogen X, irrespective of the numbering adopted for each substituent according to nomenclature rules.

Many biologically active pyridine derivatives are known, their activity pattern varying greatly according to the substituents or functional groups attached to the pyridine nucleus. Many of these compounds possess pharmacological activities and some have shown useful therapeutic applications. Very few pharmacologically active 2-halo-pyridines are known in accordance with the prior art portion of Claim 1. Some esters and amides of 2-chloronicotinic acid (French Pat. No. 1,604,911) are said to be antispasmodics and antiinflammatories (no data), and some 3-amino-2-benzoyl-6-halopyridines (German Offen. No. 2,319,872), useful as intermediates for sedatives and anxiolytics, are claimed to have these same activities and also antiphlogistic properties (no data).

Due to the undesirable side effects of the steroidal antiinflammatory drugs, there has been an intensive research for non-steroidal antiinflammatory-analgesics, or "aspirin-like" drugs, with the aim of finding not only useful antiinflammatory agents, but also in discovering non-narcotic analgesics which could have their place in the treatment of some specific but very common kinds of pain.

This effort has led to the discovery of some drugs with accepted clinical utility, but generally the safer ones have a low level of activity and the most active ones have in common a high degree of toxicity and many undesirable side effects, especially in the gastrointestinal system (bleeding, ulceration). As it is fully recognised, there is today a need for new analgesic-antiinflammatory drugs with a greater margin of safety, that is drugs with a good level of activity but with low toxicity and a low propensity to induce side-effects.

The invention as claimed provides new compounds which are intended to improve the safety margin and the therapeutic usefulness of current drugs in this area.

The compounds of the invention possess interesting pharmacodynamic properties. Specifically they have shown analgesic, antiinflammatory, antipyretic and also sedative activities in several standard animal models. As it is known, the non-steroidal antiinflammatory drugs nearly all have antiinflammatory, analgesic and antipyretic effects, but each specific substance has them in different relative intensities. The compounds of the invention usually show on an average a higher degree or level of analgesic than antiinflammatory or antipyretic activity.

This analgesic or antinociceptive activity is not related with the action of narcotic or major analgesics, as these new compounds do not show any measurable action in tests classically used for the evaluation of this class of drugs, i.e. tests in which use is made of a thermal stimulus, like the "hot-plate" test. On the contrary these compounds exhibit antinociceptive effects at low doses in tests usually employed for non narcotic analgesics or non-steroidal antiinflammatories, and also show antiinflammatory and antipyretic action in several classical animal models. At higher doses they possess also sedative or tranquilizing activities, but usually they do not show any measurable effects in the central nervous system at doses where the analgesic effect is clearly shown.

These activities coupled with a low degree of toxicity and ulcerogenic effect confer to the new compounds of the invention a great safety margin, which makes them potentially useful drugs with a high therapeutic index in the treatment of inflamatory diseases of the human and animal body, in alleviating pain almost always associated with these disorders, or in the treatment of headache, muscular pain and other kinds of peripheral pain.

Some examples of the results obtained with selected compounds of the invention in pharmacological and toxicity testing in animals will be shown.

The analgesic activity was tested using the following methods:

acetic acid writhing test in mice, according to R. Koster et. al., Fed. Proc. 18, 412 (1959), referred to as "Koster test".

antinociceptive activity in inflammed tissue of rats, according to L. O. Randall and J. J. Selitto, Arch. Int. Pharmacodyn, 111, (4) 409–19 (1957), usually known as "Randall-Selitto" test.

"hot plate" test, following the technique of G. Woolfe and A. D. McDonald, J. Pharmacol. Exptl. Ther, 80, 300–307 (1944).

Antiinflammatory activity was measured using two classical tests:

Carrageenan-induced edema in rats, by the method of C. A. Winter et. al., Proc. Soc. Exptl. Biol. Med. 111, 544–47, (1962), referred here as "Winter test".

"Cotton pellet granuloma", according to J. J. Loux et. al., Inflammation 2 (2) 125–30 (1977).

The sedative-tranquillizing effects were evaluated through the method of Holten and Larsen, Acta Pharmacol. Toxicol. 12, 346–63 (1956), modified using pentobarbital at 60 mg/Kg (i.p.) and employing as standard drug 12.5 mg/Kg diazepam (oral route). In the following this test will be mentioned as "PB sleep potentiation".

Antipyretic activity was measured in rabbits, according to the technique of Ch. A. Winter and G. W. Nuss, Toxicol. Appl. Pharmacol. 5, 247–56 (1963).

Ulcerogenic indexes were evaluated following E. Marazzi-Uberti et. al., Arzneim. Forsch. 22, 191–6 (1972).

Acute toxicities (LD50) were estimated according to L. J. Reed and H. Muench, Am. J. Hyg. 27, 493–97 (1938).

All tested compounds were administered as a suspension in aqueous 0.5% carboxymethyl cellulose. Oral route was used in all these tests, except in "hot-plate" test where the compounds were administered subcutaneously. Sprague-Dawley rats and Swiss CD 1 mice were used throughout. The following results were obtained for each specified compound:

3-benzoyl-2-chloropyridine; Koster test, ED50: 20–30 mg/kg; Winter test: 75 mg/kg have the same activity was 100 mg/kg acetylsalicylic acid.

2-chloro-3-(4-fluorobenzoyl)-pyridine; Koster test, ED50: 10–15 mg/kg; Randall-Selitto: 100 mg as active as 200 mg acetylsalicylic acid; inactive in "hot plate" test at 75 mg/kg; PB sleep potentiation: inactive at 50 mg/kg, active at 100 mg/kg; ulcerogenic index (at 100 mg/kg): 1 (control group: 1.2); LD50 (p.o. mice): aprox. 1 g/kg.

3-benzoyl-6-chloropyridine; Koster test, ED50: aprox. 30 mg/kg; PB sleep potentiation: inactive at 50 mg/kg; antipyretic activity: a dose of 200 mg/kg reduces 0.5° C. the temperature of the control group (2.7° C. mean hyperpyrexia); LD50>2 g/kg (p.o., mice).

2-chloro-α-phenyl-3-pyridinemethanol; Koster test, ED50: 18 mg/kg; Randall-Selitto, 100 mg as active as 200 mg acetylsalicylic acid; "hot plate" test, inactive at 50 and 100 mg/kg; Cotton-pellet granuloma: at 100 mg/kg, slight activity (same effects as 100 mg/kg acetylsalicylic acid); Winter test: 100 mg shows 75% the activity 100 mg acetylsalicylic acid; PB sleep potentiation, inactive at 50 mg/kg, but at 100 mg/kg shows significant activity; antipyresis, at a dose of 200 mg/kg: 40% reduction of the hyperthermia of the control group (0.9° C. reduction on a mean increment of 2.3° C.); ulcerogenic index, at 150 mg/kg: 1.5 (control group: 1.0; acetylsalicylic acid 150 mg/kg: 2.3); LD50 (p.o., mice): 1080 mg/kg; LD50 (p.o., rats): >2 g/kg.

2-chloro-α-(2,4-difluorophenyl)-3-pyridinemethanol; Koster test, ED50: 6–8 mg/kg; "hot-plate", inactive at 75 mg/kg; PB sleep potentiation, inactive at 10 mg/kg, active at 50 mg/kg; ulcerogenic index (100 mg/kg): 1.3 (control group: 1.5); LD50 (p.o., mice) 910 mg/kg; DL50 (p.o., rats): >2 g/kg.

2-chloro-α-(2,4-dichlorophenyl)-3-pyridinemethanol; Koster test, ED50: 7 mg/kg; Randall-Selitto, 100 mg/kg as active as 150 mg acetylsalicylic acid; LD50 (p.o., mice): >2 g/kg.

6-chloro-α-phenyl-3-pyridinemethanol; Koster test, ED50: 5–8 mg/kg; Winter test, 100 mg same activity as 100 mg acetylsalicylic acid (active also in adrenalectomized rats).

6-chloro-α-(4-fluorophenyl)-3-pyridinemethanol; Koster test, ED50: 5–6 mg/kg; "hot plate": inactive at 75 mg/kg; PB sleep potentiation: inactive at 50 mg/kg; ulcerogenic index (100 mg/kg): 1.6 (control group: 1.3); LD50 (p.o., mice): >2 g/kg.

3-benzoyl-2-bromopyridine; Randall-Selitto: 100 mg/kg as active as 200 mg/kg acetylsalicylic acid; "hot-plate": inactive at 75 mg/kg.

The compounds of the invention may be formulated in pharmaceutical compositions for their use in human or veterinary medicine. Within the scope of the invention are therefore included pharmaceutical compositions which have as active substances compounds of general formula I, or their physiologically acceptable salts, addition compounds or prodrugs, formulated with the aid of excipients, carriers or other conventional complementary agents. These compositions may be, for example, solid or liquid formulations for oral administration, suppositories, injections or compositions intended for topical application, such as ointments, creams or sprays. Oral administration is best achieved with formulations in the form of tablets (coated or uncoated), capsules or suspensions.

The new compounds of the invention may be obtained by general methods which as such are known in the aromatic or pyridine chemistry.

The compounds of general formula I, in which A is oxygen (formula Ia below) can be obtained by the following methods:

Method A: By reacting in Friedel-Crafts conditions an acyl halide of formula II, wherein Y is an halogen atom specially chlorine, with a compound of formula III, according to the scheme:

$$\underset{\text{(II)}}{\underset{N\quad X}{\bigcirc}\text{-COY}} + \underset{\text{(III)}}{\underset{}{\bigcirc}\text{-(R)}_n} \longrightarrow \underset{\text{(Ia)}}{\underset{N\quad X}{\bigcirc}\text{-CO-Ar}}$$

and isolating the aroyl halo-pyridines Ia formed.

In all these formulae X, Ar, n and R have the meanings defined above in formula I.

The acyl halides of formula II are obtained: (a) from the corresponding carboxylic acids (Y: OH in formula II) through reaction with inorganic acid halides, such as PCl₃, PBr₃, PCl₅ and specially SOCl₂, with or without a catalyst in a non-polar solvent and isolating the acyl halides by distillation or crystallization. The starting carboxylic acids are commercial products, such as 2-chloronicotinic acid and 6-chloronicotinic acid, or are obtained by known methods which will be referred to in the examples. (b) from pyridine carboxylic acids N-oxides by treatment with phosphorus halides or oxyhalides, such as PCl₃, PCl₅ or POCl₃; by this method acyl halides of formula II in which both halogens are identical, i.e. Y=X, are obtained.

The reagent of choice for this process is AlCl₃, using a solvent such as S₂C, nitrobenzene, nitromethane or excess of the aromatic compound of formula III itself. Reaction conditions (temperature, time or order of addition) are made according to each specific aromatic compound needed, as reactivity depends on the R substituent in the benzene nucleus. This method gave satisfactory yields and is of wide applicability, having only the known limitations of the Friedel-Crafts reaction. When one desires some specific substituents R, especially deactivating groups, or not-favoured positions for these substituents, use can be made of one of the following methods.

Method B: By reacting a nitrile of formula IV with a Grignard reagent of formula V, wherein Z is Cl, Br or I, according to the scheme

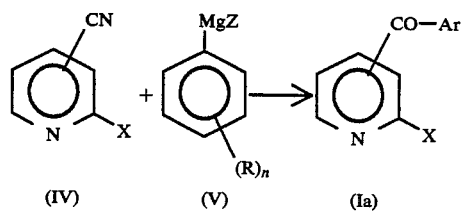

and isolating the aroyl halo-pyridines Ia after hydrolysis of the ketimine intermediate formed. In these formulae X, Ar, n and R are as defined above.

The Grignard reagents of formula V are usually prepared "in situ" by adding to a suspension of magnesium in an anhydrous solvent, usually diethyl ether, tetrahydrofuran or benzene, a compound of formula VI

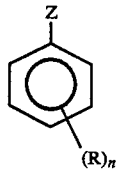

wherein n, R and Z are as defined above. The most preferred halo-aromatic compounds of formula VI are the bromo derivatives, i.e. Z=Br. Magnesium can also be substituted by other metals and use can be made also of catalysts, as is known for any expert in this field. Reaction temperatures may be in a broad range, but usually 35° to 100° are preferred in order to avoid or minimise secondary reactions.

Method C: By reacting an halo-pyridyl lithium of formula VII with an aromatic nitrile of formula VIII, according to the scheme

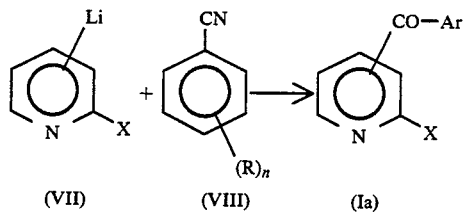

and isolating the desired aroyl-halo-pyridine Ia after hydrolysis of the intermediate formed. In all these formulae X, Ar, n and R have the meanings defined above.

Compounds of formula VII are usually obtained "in situ" by reacting an alkyl lithium, such as n-butyl lithium, with a compound of formula

wherein X is as defined above, in an inert solvent like ethyl ether or tetrahydrofuran at low temperatures.

This process can be conducted in an inert atmosphera at low temperatures, usually between −80° to 0° C., and in anhydrous conditions.

The reverse process, i.e. the reaction of an aryl lithium with an halopyridine nitrile of formula IV gives unsatisfactory yields of ketones Ia, as many secondary reactions occur.

Method D: By reacting an aroyl pyridine N-oxide of formula

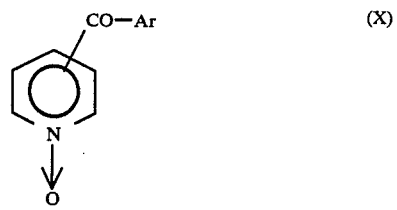

wherein Ar is as defined above, with halogenating agents such as POCl₃, POBr₃, or PCl₅ and isolating the aroylhalo-pyridines Ia formed.

The intermediate compounds formula X are obtained by treating the corresponding 2-, 3- or 4-aroyl pyridines with oxidation agents, such as peracids or hydrogen peroxide in an inert solvent like chloroform or acetic acid. The mixture hydrogen peroxide-acetic acid is usually preferred for this purpose.

This method is specially useful for obtaining compounds of formula Ia in which the substituent —CO—Ar is in 2- or 4-positions (starting from the respective 2-aroyl or 4-aroyl pyridines N-oxides) as only one isomeric halo-derivative is preferentially obtained. For example, using POCl₃ or PCl₅, 2-chloro-4-aroyl-pyridines are obtained from 4-aroyl-pyridines N-oxides, and 6-chloro-2-aroyl-pyridines when one starts with 2-aroyl-pyridines N-oxides. When the substituent —CO—Ar in formula X is in 3-position both isomeric 2-halo and 6-halo-3-aroyl-pyridines are formed. In all cases, in this deoxygenation-halogenation reaction, the halogen atom enters preferentially in a position vicinal to the nitrogen of the pyridine nucleus.

Method E: By oxidizing an α-aryl halo-pyridine methanol of general formula:

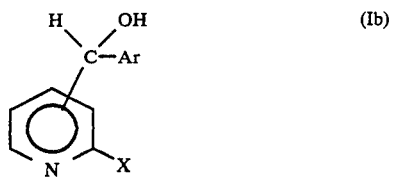

that is a compound of formula I in which A is 

by means or an inorganic or organic oxidizing agent, and isolating the aroyl halo-pyridines Ia formed. As it is known, oxidizing agents for converting secondary alcohols to ketones must be selective, usually inorganic ones like chromium trioxide, chromic acid, sodium dichromate or manganese dioxide, although also suitable are organic reagents like dimethyl sulfoxide or N-bromosuccinimide. The most usual solvents employed are acetic acid, sulfuric acid or its mixture with water, with or without a co-solvent like acetone.

Compounds of formula Ib, which are also part of this invention, can be obtained by several methods which will be described below.

A compound of formula Ia in which X=Cl can be converted to a compound of formula Ia in which X=Br by halogen exchange, usually with aqueous hydrobromic acid, although use can be made also of metal bromides like sodium bromide in an organic solvent. Hydrobromic acid is preferred in the 45-48% concentration range. If an acid-sensitive R substituent (like alkoxy) is attached to the benzene nucleus, simultaneous halogen exchange in the pyridine ring and hydrolysis of that R residue will occur.

Compounds of general formula I, in which A is 

(formula Ib above) can be obtained by the following methods:

Method F: By reacting an halo-pyridyl lithium of formula VII (see above) with an aromatic aldehyde ArCHO, wherein Ar is as above, and isolating the desired compound formula Ib, after hydrolysis of the labile intermediate formed.

Compounds formula VII are prepared as described before (method C). Reaction conditions are also similar to those specified there.

It is also possible to make use of the reverse process, that is: reaction of an aryl lithium with an halo-pyridine carboxaldehyde of a structure like that of formula IV (substituting —CHO for —CN), but this process offers the disadvantage of the difficult accessibility of these intermediate aldehydes.

Method G: By reducing an aroyl halo-pyridine of formula Ia with metal hydrides, especially NaBH$_4$ and LiAlH$_4$ in an inert organic solvent and in anhydrous conditions, and isolating the α-aryl halo-pyridinemethanol Ib formed.

Using NaBH$_4$, alcohols can be used as solvents, the preferred one being ethyl alcohol, and if LiAlH$_4$ is used, ethyl ether, diethyleneglycol dimethyl ether or pyridine are suitable.

Although other reducing agents can substitute for metal hydrides, these have the advantage of reducing selectively the ketone function almost without any effect in the pyridine nucleus or the halogen atom.

Compounds of formula I can be converted to other simple derivatives useful for changing their solubility, as addition or saltlike compounds, or for modifying their absorption pattern, like esters of compounds Ib with some organic acids. For this purpose one can use organic acid moieties which are physiologically acceptable, without significant pharmacological activity, and easily hydrolysable, like acetic, succinic or other acid moieties usually employed in prodrug pharmaceutical chemistry.

Compounds of general formula I which have an asymmetric carbon atom, such as secondary alcohols Ib, and which are generally obtained as racemic mixtures, can be resolved in their optical isomers by some of the methods commonly used for the resolution of alcohols; or a specific optical isomer can be prepared by means of an asymmetric synthesis, although it is difficult to achieve a high degree of optical purity, as is common with organic compounds having two similar bulky aryl rings linked to the asymmetric carbon of a carbinol group.

The invention is illustrated with some representative examples; throughout them, melting points are those observed in a micro hot-stage (KOFLER). Microanalysis data refers to percentage found, followed by the calculated value in parentheses, i.e. "Cl 15.97 (16.29)" means: found 15.97% chlorine (calculated 16.29%).

EXAMPLE 1

3-benzoyl-2-chloro-pyridine (a) 200 g 2-chloro-nicotinic acid and 600 ml thionyl chloride are refluxed 5 hrs. Excess thionyl chloride is eliminated in a rotary evaporator (water pump) and the residue is distilled in vacuo at 160°-4° C., collecting an oil which spontaneously crystallises. Yield: 210 g 2-chloro-nicotinyl chloride m.p. 56° C.

(b) To a cooled solution of 150 g 2-chloro-nicotinoyl chloride in 400 ml benzene there is added slowly 238 g AlCl$_3$. After refluxing 2 hrs. the reaction mixture is added with stirring to a slightly acidic ice: water mixture. The organic layer is separated and the aqueous one is extracted with ethyl ether. The combined organic layers are washed with HONa 1N, then with water, and dried over Na$_2$SO$_4$. The excess benzene is distilled at water pump pressure in a rotary evaporator and the residual oil is distilled in vacuo. Yield: 157 g of title product, b.p. 123° C./0.05 mm; m.p. 35°-7° C.; UV (ethanol): λmax. 254 nm., ε: 17,180; Cl 15.97 (16.29).

EXAMPLE 2

Reacting 2-chloro-nicotinoyl chloride as in Example 1 with an excess of
(a) 1,3,5-trimethylbenzene.
(b) fluorobenzene.
(c) 1,3-difluorobenzene.
(d) chlorobenzene.
(e) 1,3-dichlorobenzene.

there are obtained the following compounds
(a) 2-chloro-3-(2,4,6-trimethylbenzoyl)-pyridine, m.p. 59°-60° C.; Cl 13.57 (13.66).
(b) 2-chloro-3-(4-fluorobenzoyl)-pyridine, m.p. 73°-4° C.; Cl 15.21 (15.05); F 8.06 (8.06).
(c) 2-chloro-3-(2,4-difluorobenzoyl)-pyridine, m.p. 63°-4° C.; Cl 14.02 (13.98); F 14.32 (14.98).
(d) 2-chloro-3-(4-chlorobenzoyl)-pyridine, m.p. 60°-3° C.; Cl 27.65 (28.13).
(e) 2-chloro-3-(2,4-dichlorobenzoyl)-pyridine, as an oil, b.p. 140°-5° C./10$^{-3}$ mm; Cl 37.25 (37.12).

EXAMPLE 3

2-chloro-4-(4-fluorobenzoyl)-pyridine (a) 226 g isonicotinic acid N-oxide, 454 g PCl$_5$ and 683 g POCl$_3$ are heated with stirring at 60° C. and then refluxed 3 hrs. Excess POCl$_3$ is distilled first at atmospheric and then at reduced pressure. The reaction mixture is added with stirring to slightly alkaline (pH ca. 8) water, and aqueous NaOH is added until pH=3. The solid formed is filtered and washed with ethanol and ether. Yield: 171 g 2-chloro-isonicotinic acid, m.p. 240°-2° C.

(b) 171 g 2-chloro-isonicotinic acid and 760 ml SOCl$_2$ are refluxed 24 hrs. Excess SOCl$_2$ is distilled off at reduced pressure and the last traces are azeotropically distilled with benzene. The residual oil is distilled in vacuo. Yield: 160 g 2-chloro-isonicotinoyl chloride, b.p. 101° C./10 mm.

(c) 10 g isonicotinic acid N-oxide, 20 g PCl$_5$ and 30 g POCl$_3$ are refluxed 2.5 hrs. After distilling excess POCl$_3$, the crude oil is fractionally distilled at reduced pressure. Yield: 3.5 g 2-chloro-isonicotinoyl chloride, which by gas chromatography is identical with that obtained in (b).

(d) To a solution of 4.2 g 2-chloro-isonicotinoyl chloride in 25 ml. fluorobenzene there is added with cooling 11.7 g AlCl$_3$. The mixture is heated at 70°-80° C. during 7 hrs. The crude is added to acidic (pH 1-2) cold water. The pH is raised until 4.5 with diluted aqueous NaOH. This aqueous organic mixture is extracted several times with methylene chloride. The combined extracts are washed with water, dried (Na$_2$SO$_4$) and distilled in a rotary evaporator. The remaining crude oil is purified through a silica column, eluting with ethyl ether:petroleum ether 1:3. Yield 5 g of the title product, m.p. 60°-3° C. (cyclohexane); UV (ethanol) λmax.: 262 nm, ε=10,250; Cl 15.30 (15.05); F 8.15 (8.06).

EXAMPLE 4

Similary as described in exs. 1 or 3 and reacting 2-chloroisonicotinoyl chloride with an excess of the appropriate aromatic product, there are also obtained the following 4-aroyl-substituted compounds:
4-benzoyl-2-chloro-pyridine, m.p. 38°-41° C.; b.p. 125°-9° C./0.07 mm.
2-chloro-4-(2,4-difluorobenzoyl)-pyridine, m.p. 50°-3° C.; Cl 14.07 (13.98).
2-chloro-4-(4-chlorobenzoyl)-pyridine, m.p. 85°-6° C.
2-chloro-4-(2,4-dichlorobenzoyl)-pyridine, m.p. 98°-9° C.; Cl 37.68 (37.12).

EXAMPLE 5

3-aroyl-6-chloro-pyridines (a) Starting from 250 g 6-chloro-nicotinic acid and 850 ml SOCl$_2$, and using the working conditions as in Ex. 1a, there is obtained 243 g 6-chloronicotinoyl chloride, m.p. 49°-51° C.; b.p. 75° C./0,05 mm.

(b) Reacting, in similar conditions as in Exs. 1 or 3, 6-chloronicotinoyl chloride with benzene, 1,4-dimethyl benzene, 1,3,5-trimethylbenzene, fluorobenzene, chlorobenzene, 1,3,-dichlorobenzene or 1,3-difluorobenzene there are respectively obtained the following compounds:
3-benzoyl-6-chloro-pyridine, m.p. 53°-5° C.; Cl 15.92 (16.29).
6chloro-3-(2,5-dimethylbenzoyl)-pyridine, m.p. 60°-2° C.; Cl 14.74 (14.43).
6-chloro-3-(2,4,6-trimethylbenzoyl)-pyridine, m.p. 65°-8° C.; Cl 13.44 (13.66).
6-chloro-3-(4-fluorobenzoyl)-pyridine, m.p. 88°-9° C.; Cl 15.10 (15.05); F 8.13 (8.06).
6-chloro-3-(4-chlorobenzoyl)-pyridine, m.p. 129° C.; Cl 27.85 (28.13).
6-chloro-3-(2,4-dichlorobenzoyl)-pyridine, m.p. 79°-80° C.; Cl 37.69 (37.12).
6-chloro-3-(2,4-difluorobenzoyl)-pyridine, m.p. 56°-7° C. (n-hexane); Cl 14.00 (13.98); F 15.03 (14.98).

EXAMPLE 6

6-chloro-2-(2,4-dichlorobenzoyl)-pyridine (a) 137 g NaNO$_2$ is added to 100 g 2-amino-6-methylpyridine is 2 ls conc. HCl at −20° C. After 1 hr. at this temperature, the reaction mixture is basified with 10N NaOH and extracted with ethyl ether. The organic phase is washed with water, dried and solvent removed in a rotary evaporator. Yield: 80 g crude 2-chloro-6-methylpyridine, as an oil, used as such in the next step.

(b) To a well-stirred suspension of 57.7 g 2-chloro-6-methylpyridine in 800 ml water there is added a solution of 122 g KMnO$_4$ in 1.1 ls water. The mixture is heated until the purple colour disappears. The same amount of KMnO$_4$ is added now and heating is continued until no colour remains. After steam-distillation of the reaction mixture, 10 g of unreacted starting product is recovered. The hot suspension is filtered through diatiomaceous earth (CELITE). The clear water solution is concentrated until about 1 l volume. Adding conc. HCl with stirring, a white solid is formed. The suspension is filtered after cooling. The filtrate is concentrated and filtered several times. Yield: 60 g 6-chloro-2-pyridinecarboxylic acid, m.p. 192°-4° C., after crystallisation from water.

(c) A mixture of 40 g 6-chloro-2-pyridinecarboxylic acid and 150 ml SOCl$_2$ is refluxed 4 hrs. After removing excess SOCl$_2$ there is obtained 44 g 6-chloro-2-pyridinecarboxylic acid chloride, m.p. 76° C.

(d) 40.9 g AlCl$_3$ is added in portions to a mixture of 26.4 g 6-chloro-2-pyridinecarboxylic acid chloride and 112 g 1,3-dichlorobenzene. The mixture is slowly heated until 130°-40° C. After standing overnight, it is added to a mixture of diluted HCl and crushed ice, basified and extracted with ethyl ether. The ethereal extracts are washed with water, dried and solvent evaporated (water pump). The residual deep green oil is crystallised from ethanol:water in the presence of decolorizing carbon. Yield: 10 g title compound, m.p. 103°-4° C.; UV (ethanol): λmax. 281 nm; ε: 14,500; Cl 37.02 (37.12).

EXAMPLE 7

By the same method of ex. 6 there are also obtained:

2-benzoyl-6-chloropyridine, m.p. 55°–6° C.; Cl 16.26 (16.29).
6-chloro-2-(4-fluorobenzoyl)-pyridine, m.p. 79°–80° C.; Cl 15.20 (15.05); F 8.00 (8.06).
6-chloro-2-(2,4-difluorobenzoyl)-pyridine, m.p. 102°–3° C. (methanol:water); Cl 14.16 (13.98); F 15.11 (14.98).

EXAMPLE 8

2-chloro-3-(4-phenylbenzoyl)-pyridine 26.7 g AlCl$_3$ is added slowly while stirring to a solution of 9.2 g biphenyl and 10.6 g 2-chloronicotinoyl chloride in 170 ml carbon disulfide. The mixture is refluxed 5 hrs. After cooling, the S$_2$C layer is poured off, and the residue is added to acidic ice:water, basified and extracted with methylene chloride. The combined extracts are washed, dried (MgSO$_4$) and solvent removed in vacuo. The crude product is chromatographed on a silicagel column and eluted with benzene:ethyl acetate 15:1 Yield: 5 g of title product, m.p. 128°–32° C.; UV (ethanol): λmax. 295 nm, ε: 27,260; Cl 11.96 (12.07).

EXAMPLE 9

Using similar working conditions as in ex. 8, and reacting 2-chloronicotinoyl chloride with 1,4-dimethylbenzene, tert-butyl-benzene, anisole or thioanisole, there are also obtained:
2-chloro-3-(2,5-dimethylbenzoyl)-pyridine, as an oil b.p. 140°–4° C./0.1 mm; Cl 14.34 (14.43).
3-(4-tert-butyl-benzoyl)-2-chloro-pyridine, as a viscous oil; Cl 12.82 (12.95).
2-chloro-3-(4-methoxybenzoyl)-pyridine, m.p. 74°–6° C.
2-chloro-3-(4-methylthiobenzoyl)-pyridine, m.p. 89°–90° C.; UV (ethanol): λmax. 326 nm, ε: 20,650; Cl 13.55 (13.44); S 12.19 (12.16).

Similarly, starting from 2-chloro-isonicotinoyl chloride and the appropriate substituted benzene, there are obtained;
2-chloro-4-(2,5-dimethylbenzoyl)-pyridine, as an oil, b.p. 132°–6° C./0.05 mm; Cl 14.45 (14.43).
4-(4-tert-butyl-benzoyl)-2-chloro-pyridine, as a viscous oil; Cl 13.36 (12.95).
2-chloro-4-(4-phenylbenzoyl)-pyridine, m.p. 122°–3° C.; UV (ethanol): λmax. 299; ε: 22,525; Cl 12.15 (12.07).

Starting from 6-chloro-2-pyridinecarboxylic acid chloride and 2,4-dimethylbenzene, and using also the reaction conditions of ex. 8, there is obtained:
6-chloro-2-(2,5-dimethylbenzoyl)-pyridine, m.p. 35°–7° C.; b.p. 140°–5° C./0.5 mm; Cl 14.80 (b 14.43).

EXAMPLE 10

3-benzoyl-2-chloro-pyridine

A solution of 3.14 g (0.02 mols) bromobenzene in anhydrous ether is added dropwise to a suspension of 0.02 mols magnesium in anhydrous ether. The mixture is refluxed 1.5 hr. and is then cooled until room temperature. Now a solution of 1:38 g 2-chloro-3-cyanopyridine in 25 ml anhydrous ether is added slowly while stirring. The reaction mixture is refluxed 24 hrs. and there is added, after standing, 10% aqueous HCl. The aqueous layer is separated and the ethereal layer is washed with 25% aqueous HCl. The combined washings and the first aqueous layer are basified with 40% NaOH and extracted with ether. The combined extracts are dried (MgSO$_4$) and solvent evaporated. The crude is distilled in vacuo. Yield: 0.8 g of title product, identical with that described in Ex. 1b.

EXAMPLE 11

4-benzoyl-2-chloropyridine

A mixture of 2.5 g 4-benzoylpyridine N-oxide m.p. 127°–30° C. (obtained according to T. KATO et. al., Yakugaku Zasshi 86, 1022–26, 1966), and 6 ml phosphorus oxychloride is refluxed for 2 hrs. After cooling, the reaction mixture is very slowly added to ice:water, basified (10N NaOH) and extracted with methylene chloride. The organic layer is washed with water, dried and solvent removed in a rotary evaporator. Yield: 2.4 g of title product, identical with that described in Ex. 4.

EXAMPLE 12

2-chloro-4-(4-fluorobenzoyl)-pyridine (a) 5 g 4-(4-fluorobenzoyl)-pyridine (M. P. BREEN, et. al., J. Pharm. Sci. 62, 847–9, 1973), 50 ml 30% H$_2$O$_2$ and 25 ml glacial acetic acid are heated at 60° C. for 8 hrs.

The solvent is distilled in vacuo and the residue extracted with methylene chloride. The organic extracts are dried and solvent removed in a rotary evaporator. The crude oil is crystallised from ethanol. Yield: 1.6 g 4-(4-fluorobenzoyl)-pyridine N-oxide, as white crystals m.p. 158°–9° C.; F 8.65 (8.75).

(b) 0.88 g 4-(4-fluorobenzoyl)-pyridine N-oxide and 50 ml POCl$_3$ are refluxed for 2 hrs. Excess POCl$_3$ is distilled at normal pressure. The crude is treated with slightly alkaline cold water and then extracted with methylene chloride. Working as usual affords 0.80 g of title product, identical with that obtained by the Friedel-Crafts process (see Ex. 3d).

EXAMPLE 13

2-benzoyl-6-chloro-pyridine 1.5 g 2-benzoyl-pyridine N-oxide (T. Kato et. al., see reference in Ex. 11) and 3.6 ml POCl$_3$ are refluxed for 25 minutes. The cooled mixture is added to slightly alkaline ice:water, extracted with chloroform, the organic extract dried and solvent removed in vacuo. Yield: 1.1 g of title product, which by thin layer and gas chromatography is identical with that described in Ex. 7.

EXAMPLE 14

6-bromo-3-(4-fluorobenzoyl)-pyridine 2.35 g 6-chloro-3-(4-fluorobenzoyl)-pyridine (see Ex. 5) and 50 ml 47% aqueous HBr are refluxed for 1 hr. After this time a control by gas chromatography reveals no starting chloro-derivative is present. The reaction liquid is added to water, and a yellow solid is formed. The mixture is basified with concentrated NaOH, and the crystalline solid is filtered and recrystallised from methanol:water. Yield: 0.9 g title product, as white crystals, m.p. 97°–8° C.; UV (water): λmax. 278 nm, ε: 16,600; Br 28.34 (28.53); F 7.11 (6.78).

EXAMPLE 15

Similary as in ex. 14, and starting from the respective aroyl chloropyridines described in previous examples, the following aroyl bromo-pyridines are obtained:
3-benzoyl-2-bromopyridine, m.p. 47°–50° C.; Br 30.59 (30.49).
4-benzoyl-2-bromopyridine, m.p. 53°–4° C.
2-bromo-4-(2,5-dimethylbenzoyl)-pyridine, as an oil.

3-benzoyl-6-bromopyridine, m.p. 67°–9° C.; Br 30.16 (30.49).

2-benzoyl-6-bromopyridine, m.p. 61°–2° C.; Br 30.12 (30.49).

EXAMPLE 16

2-bromo-3-(4-hydroxybenzoyl)-pyridine 4 g 2-chloro-3-(4-methoxybenzoyl)-pyridine (see ex. 9) and 40 ml 47% aqueous HBr are refluxed for 3 hrs. Excess HBr is distilled off and the residue is added to water. The mixture is extracted with ether, the ethereal extracts are dried and solvent removed in a rotary evaporator. The crude oil is seen to be by gas chromatography a mixture of the desired product and 2-chloro-3-(4-hydroxybenzoyl)-pyridine in 50%:50% proportion.

0.5 g of this mixture and 5 ml 47% HBr is refluxed for three days. The crude is treated as before, affording 0.15 g of title product, as an oil which by gas chromatography shows a content greater than 90%.

EXAMPLE 17

2-chloro-α-(3-methoxyphenyl)-3-pyridinemethanol 71.5 ml of a 2.1N solution of n-butyllithium in hexane are added to 19.2 g 3-bromo-2-chloropyridine (obtained according to J. D. Cook et. al. J. Chem. Soc., Section C, 1969 1973–8) in 300 ml anhydrous ether at −60° C. and under a static nitrogen atmosphere. To this freshly prepared solution of 2-chloro-3-pyridyllithium, a solution of m-anisaldehyde (13.6 g) in 100 ml anhydrous ether is added dropwise. The reaction mixture is stirred for 1 hr. at −60° C. and then is added to ice:water. The organic phase is separated and the aqueous phase is extracted with ether. The combined organic solutions are washed with water, dried (MgSO$_4$) and solvent evaporated. The crude oil is chromatographed over SiO$_2$ and eluted with chloroform, obtaining 14.9 g of title product as an oil which spontaneously crystallises. Recrystallisation from methanol:water affords pure product, m.p. 114°–5° C.; Cl 14.65 (14.20).

EXAMPLE 18

6-bromo-α-(3-phenoxyphenyl)-2-pyridinemethanol

By the same procedure of Ex. 17, reacting 3-phenoxybenzaldehyde (19.8 g in 100 ml ether) with 6-bromo-2-pyrdillithium (from 23.7 g 2,6-dibromopyridine in 400 ml. ether and 71.5 ml 2.1N n-butyllithium), there is obtained a yellow oil which is chromatographed on SiO$_2$ and eluted with ether:petroleum ether 1:1. Yield: 29.5 of title product, as an oil, which by thin layer chromatography shows a unique spot. Br 22.83 (22.43).

EXAMPLE 19

6-bromo-α-(2-methoxyphenyl)-2-pyridinemethanol

Similarly as in Ex. 17 and 18, and starting from o-anisaldehye (13.6 g) and 2,6-dibromopyridine (23.7 g) there is obtained 5.2 g title product, as a white solid m.p. 96°–8° C. (cyclohexane); Br 27.11 (27.16).

EXAMPLE 20

2-chloro-α-phenyl-3-pyridinemethanol (a) Ketone reduction with NaBH$_4$:

Sodium borohydride (8.5 g) is added slowly to a stirred mixture of 25 g 3-benzoyl-2-chloropyridine (see Ex. 1) in 200 ml anhydrous ethanol. After 1 hr. at room temperature, the solvent is removed in vacuo. The residue is mixed with water, acidified and extracted with chloroform. The organic phase is dried and solvent distilled in a rotary evaporator. Yield: 22.8 g title product, m.p. 90° C.; Cl 16.24 (16.14).

(b) Ketone reduction with LiAlH$_4$:

2.4 g lithium aluminium hydride is added very slowly to 10.6 g 3-benzoyl-2-chloropyridine in 100 ml anhydrous pyridine. After stirring for 2 hrs. at room temperature, the solvent is distilled in vacuo, the residue is added to 5% aqueous HCl and extracted with ether. Working as usual there is obtained 4.5 g of a product, identical with that obtained as in (a).

EXAMPLE 21

Similary, by the process of Ex. 20(a) or (b) and starting from the appropriate ketones (obtained as in Ex. 1 to 15), the following α-aryl-halo-pyridinemethanols are obtained:

(a) with NaBH$_4$ as reductive agent:

2-chloro-α-(4-tert-butyl-phenyl)-3-pyridinemethanol, m.p. 135°–7° C.; Cl 12.45 (12.86).

2-chloro-α-(4-fluorophenyl)-3-pyridinemethanol, m.p. 94°–5° C.; Cl 14.65 (14.92); F 8.04 (7.99).

2-chloro-α-(2,4-difluorophenyl)-3-pyridinemethanol, m.p. 96°–7° C.; Cl 14.00 (13.87); F 15.13 (14.86).

2-chloro-α-(2,4-dichlorophenyl)-3-pyridinemethanol, m.p. 138°–9° C.; Cl 36.84 (36.86).

2-chloro-α-(4-methylthiophenyl)-3-pyridinemethanol, m.p. 97°–99° C.; Cl 13.47 (13.34); S 11.99 (12.06).

2-chloro-α-(4-fluorophenyl)-4-pyridinemethanol, m.p. 110°–12° C.; Cl 15.13 (14.92); F 8.15 (7.99).

6-bromo-α-(4-fluorophenyl)-3-pyridinemethanol, m.p. 60°–2° C.; Br 28.64 (28.33); F 6.73 (6.73).

6-chloro-α-(4-fluorophenyl)-3-pyridinemethanol, m.p. 91°–2° C.; Cl 14.71 (14.92); F 7.72 (7.99).

6-chloro-α-(2,4-difluorophenyl)-3-pyridinemethanol, m.p. 73°–5° C.; Cl 13.78 (13.87); F 14.87 (14.86).

6-chloro-α-(2,4-dichlorophenyl)-3-pyridinemethanol, as an oil; Cl 36.57 (36.86).

6-chloro-α-phenyl-2-pyridinemethanol, m.p. 58°–60° C.; Cl 16.21 (16.14).

6-chloro-α-(2,5-dimethylphenyl)-2-pyridinemethanol, m.p. 90°–1° C.; Cl 14.83 (14.31).

6-chloro-α-(4-fluorophenyl)-2-pyridinemethanol, as an oil; Cl 15.38 (14.92); F 7.76 (7.99).

6-chloro-α-(2,4-difluorophenyl)-2-pyridinemthanol, as an oil; Cl 14.05 (13.87); F 14.99 (14.86).

6-chloro-α-(2,4-dichlorophenyl)-2-pyridinemethanol, m.p. 86°–8° C.; Cl 36.38 (36.86).

(b) With LiAlH$_4$ as reductive agent:

2-chloro-α-(2,5-dimethylphenyl)-3-pyridinemethanol, m.p. 127°–30° C.; Cl 14.25 (14.31).

2-chloro-α-(2,4,6-trimethylphenyl)-3-pyridinemethanol, m.p. 125°–6° C.; Cl 13.43 (13.55).

2-chloro-α-(4-chlorophenyl)-3-pyridinemethanol, m.p. 105°–7° C.; Cl 27.70 (27.90).

2-chloro-α-(4-methoxyphenyl)-3-pyridinemethanol, m.p. 128°–9° C.; Cl 14.36 (14.20).

2-chloro-α-phenyl-4-pyridinemethanol, m.p. 95°–6° C.; Cl 16.05 (16.14).

2-chloro-α-(2,5-dimethylphenyl)-4-pyridinemethanol, m.p. 110°–1° C.; Cl 13.97 (14.31).

2-chloro-α-(4-chlorophenyl)-4-pyridinemethanol, m.p. 140°–1° C.; Cl 27.83 (27.90).

2-chloro-α-(2,4-dichlorophenyl)-4-pyridinemethanol, m.p. 162°–4° C.; Cl 36.84 (36.86).

6-chloro-α-phenyl-3-pyridinemethanol, m.p. 58°–9° C.; Cl 16.17 (16.14).

6-chloro-α-(4-chlorophenyl)-3-pyridinemethanol, m.p. 126°-8° C.; Cl 27.48 (27.90).

EXAMPLE 22

6-bromo-2-(3-phenoxybenzoyl)-pyridine

A solution of 5 g chromium trioxide in 10 ml water is added to a mixture of 20 g 6-bromo-α-(3-phenoxyphenyl)-2-pyridinemethanol (see Ex. 18) and 70 ml glacial acetic acid. After stirring for 1 hr. at room temperature, the reaction mixture is added to ice:water and extracted with chloroform. The organic layer is washed with 2.5N NaOH, then with water, dried ($Na_2SO_4$) and solvent removed. Yield: 15.4 g of the title product, m.p. 65°-6° C. (from methanol); Br 22.87 (22.56).

EXAMPLE 23

6-bromo-2-(2-methoxybenzoyl)-pyridine

By the same procedure of Ex. 22, and reacting 3.3 g 6-bromo-α-(2-methoxyphenyl)-2-pyridinemethanol (obtained as in Ex. 19) in 20 ml glacial acetic acid with $CrO_3$ (1 g in 5 ml water), there is obtained 2.17 g title product, m.p. 97°-8° C. (ethanol:water); UV (ethanol): λmax. 278 nm, ε: 12,480; Br 27.67 (27.36).

EXAMPLE 24

Similarly as in Exs. 22 and 23, and starting from 2-chloro-α-(3-methoxyphenyl)-3-pyridinemethanol (see Ex. 17), there is also obtained: 2-chloro-3-(3-methoxybenzoyl)-pyridine, m.p. 50°-2° C.; Cl 14.51 (14.34).

EXAMPLE 25

2-chloro-α-phenyl-3-pyridinemethanol acetate

A mixture of 4.39 g 2-chloro-α-phenyl-3-pyridinecarboxylic (see Ex. 20), 3.14 g acetyl chloride and 8 ml trifluoroacetic acid is stirred for 1 hr. at room temperature. The reaction liquid is added dropwise to water, and the solid formed is filtered, washed, dried and crystallised from cyclohexane. Yield: 4.46 g title product, m.p. 100°-2° C.; Cl 13.82 (13.55).

EXAMPLE 26

2-chloro-α-phenyl-3-pyridinemethanol monophthalate 0.37 g phthalic anhydride, 0.50 g 2-chloro-α-phenyl-3-pyridinemethanol and 3 ml pyridine are heated at 100° C. for 7 hrs. The reaction mixture is diluted with ether and extracted twice with aqueous sodium carbonate. The aqueous extracts, after washing with ether, are acidified with 2N HCl, affording 0.5 g title product, m.p. 173°-4° C. (ethanol:water); neutralization equivalent: 372 (calculated 367.8); Cl 9.73 (9.64).

EXAMPLE 27

To prepare 10,000 tablets each containing 100 mg active ingredient: Sieve and mix together 1,000 g active ingredient and 1,740 g lactose USP. Then add to this mixture a solution of 60 g polyvinylpyrrolidone in 600 ml 96% ethyl alcohol, mix well to produce a damp cohesive mass, granulate and dry. Granulate again to obtain 0.5 mm particles. Add a sieved mixture of 100 g talc, 50 g magnesium stearate, 30 g carboxymethylstarch and 20 g sodium laurylsulfate, mix together and compress by a suitable tableting press machine using 10 mm. diameter punches to obtain tablets each weighing 300 mg.

The compounds claimed herein are also intermediates for the preparation of other pharmaceutically valuable compounds since they contain several reactive functional groups.

What is claimed is:

1. A 2-halo-pyridine of the formula:

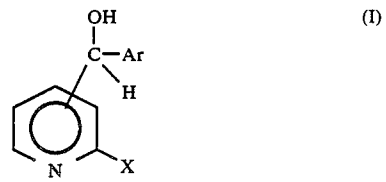

wherein X is Cl or Br; Ar is phenyl or substituted phenyl of the formula

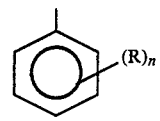

in which n is 0, 1, 2 or 3; R is $C_{1-4}$ alkyl, $C_{1-4}$ alkoxy, phenoxy, $C_{1-4}$ alkylthio, halogen, OH or $C_6H_5$; or a pharmaceutically acceptable salt thereof.

2. The 2-halo-pyridine compound of claim 1, wherein halogen is F or Cl.

3. The 2-halo-pyridine compound of claim 1, wherein the alcohol-containing substituent on the pyridine ring is located at the 3 4, 5 or 6 position of the pyridine ring relative to the X substituent.

4. The 2-halo-pyridine compound of claim 1, wherein Ar is selected from the group consisting of 3-methoxyphenyl; 3-phenoxyphenyl; 2-methoxyphenyl; phenyl; 4-t-butyl-phenyl; 4-fluorophenyl; 2,4-difluorophenyl; 2,4-dichlorophenyl; 4-methylthiophenyl; 2,5-dimethylphenyl; 2,4,6-trimethylphenyl; and 4-chlorophenyl and n is 1.

* * * * *